United States Patent
Roser

(10) Patent No.: US 7,244,825 B2
(45) Date of Patent: *Jul. 17, 2007

(54) DRIED BLOOD FACTOR COMPOSITION TREHALOSE

(75) Inventor: Bruce Joseph Roser, Cambridgeshire (GB)

(73) Assignee: Quadrant Drug Delivery Limited, Nottingham (GB)

(*) Notice: Subject to any disclaimer, the term of this patent is extended or adjusted under 35 U.S.C. 154(b) by 289 days.

This patent is subject to a terminal disclaimer.

(21) Appl. No.: 10/658,219

(22) Filed: Sep. 8, 2003

(65) Prior Publication Data

US 2005/0192216 A1    Sep. 1, 2005

Related U.S. Application Data

(63) Continuation of application No. 09/888,734, filed on Jun. 25, 2001, which is a continuation of application No. 08/875,796, filed as application No. PCT/GB96/00119 on Jan. 19, 1996, now Pat. No. 6,649,386.

(30) Foreign Application Priority Data

Jan. 19, 1995  (GB)  ................................. 9501040.1

(51) Int. Cl.
*A61K 35/14* (2006.01)
*C07K 1/00* (2006.01)

(52) U.S. Cl. ................. 530/383; 530/381; 530/384

(58) Field of Classification Search ................ 435/212, 435/2; 514/777, 53; 530/380, 381, 382, 530/383, 384; 517/777, 53
See application file for complete search history.

(56) References Cited

U.S. PATENT DOCUMENTS

| | | | |
|---|---|---|---|
| 4,495,175 A | 1/1985 | Chavin et al. | |
| 4,758,657 A | 7/1988 | Farb et al. | |
| 4,806,343 A | 2/1989 | Carpenter et al. | |
| 4,891,319 A | 1/1990 | Roser | |
| 5,288,853 A | 2/1994 | Bhattacharva et al. | |
| 5,364,756 A | 11/1994 | Livesey et al. | |
| 5,565,427 A | 10/1996 | Freudenberg | |
| 5,576,291 A | 11/1996 | Curtis | |
| 5,824,780 A | 10/1998 | Curtis et al. | |
| 6,586,573 B1 | 7/2003 | Besman et al. | |
| 6,649,386 B2 | 11/2003 | Roser | |

FOREIGN PATENT DOCUMENTS

| | | |
|---|---|---|
| EP | 0 314 095 A1 | 5/1989 |
| EP | 0 315 968 | 5/1989 |
| EP | 0 475 409 A2 | 3/1992 |
| WO | WO 87/00196 | 1/1987 |
| WO | WO 94/07510 A1 | 4/1994 |
| WO | WO 95/01804 | 1/1995 |
| WO | WO 95/07713 | 3/1995 |

OTHER PUBLICATIONS

Cleland, J.L. et al. (ed) "Design and Development Strategies" Chapter 1 in Formulation and Delivery of Proteins and Peptides, American Chemical Society Symposium Series (1994) 567:1-19.
Roser, B. et al. "Trehalose Drying: A Novel Replacement for Freeze-Drying" BioPharm (Sep. 1991) vol. 4(8):47-53.
"AlphaNine SD/Alphanate/Profilnine SD" Internet Citation, <URL:htttp://www.alphather.com/products/ins_alpha.htm>, retrieved on Jul. 19, 1999 1 page.
Bundesverband der Pharmazeutishcen Industrie E.V.: 'Rote Liste 1994', Editio Cantor, Aulendorf/Wurtt., DE (1994) Monographs 47 021 and 47 022 and an English Translation of relevant sections thereof.
Colaco et al., Bio/Technology (1992) 10(9):1007-1011.
Communication from the European Patent Office for EP 03 002 147.1, dated Nov. 15, 2006, 1 page.

*Primary Examiner*—Ruth A Davis
(74) *Attorney, Agent, or Firm*—Morrison & Foerster LLP

(57) ABSTRACT

A stable blood factor composition contains a stabilising amount of trehalose in the absence of human serum albumin to provide a product stable at up to 60° C.

14 Claims, No Drawings

DRIED BLOOD FACTOR COMPOSITION TREHALOSE

CROSS-REFERENCE TO RELATED APPLICATIONS

This application is a continuation application of co-pending application U.S. Ser. No. 09/888,734, filed Jun. 25, 2001; which is a continuation application of U.S. Ser. No. 08/875,796, filed Oct. 30, 1998, now U.S. Pat. No. 6,649, 386, which was filed as a National Stage Application of International Application Number PCT/GB96/00119, filed Jan. 19, 1996, published, pursuant to PCT Article 21(2); which claims priority to Great Britain Application GB 9501040.1, Jan. 19, 1995.

BACKGROUND OF THE INVENTION

This invention relates to dried compositions of blood factors for reconstitution with water or aqueous solutions.

Blood factors, particularly factor VIII and factor IX, are now the standard treatment for diseases caused by a lack of the appropriate factor, in particular haemophilia. The blood factor has generally been derived from human blood by various extraction techniques, for example as disclosed in EP-A-0083483, or by expression in genetically modified microorganisms, for example as disclosed in EP-A-0160457 and EP-A-0182448.

Blood factor products such as factor VIII are highly delicate, unstable proteins. They are usually supplied in the form of frozen solutions in an appropriate buffer or, more generally, as freeze-dried powders. Even the freeze-dried powders must be kept cold during storage. In order to stabilise the freeze-dried material, commercial products contain a stabilising protein, in particular human serum albumin (HSA). It has not been thought possible to prepare a dry blood factor composition which is stable at ambient temperatures and at pasteurisation temperatures (e.g. 60° C.) in the absence of HSA. However, the presence of HSA introduces considerable problems of purification since it is essential that the protein is free of viral contamination. The use of recombinant HSA to overcome these problems is expensive.

Trehalose is known to be a highly effective stabilising agent for delicate proteins, as disclosed in U.S. Pat. No. 4,891,319, enabling proteins to be dried at temperatures above freezing. We have now found that if trehalose is used to stabilise a blood factor product, not only can the product be dried with or without freezing, but also the product is stable even when retained at a temperature of 60° C. for an extended period, in the complete absence of HSA. According to the present invention therefore we provide a stable dried blood factor composition containing a stabilising amount of trehalose in the absence of albumin.

In general, any stabilising amount of trehalose may be used and an excess in general causes no problems. Indeed, the presence of trehalose aids the rehydration process and is physiologically acceptable for injection, being rapidly metabolised to glucose. The composition is particularly suited to formulations of factor VIII, which may also contain appropriate buffering and ion-reinforcing salts, in particular a source of calcium. In general, a ratio of about 1.0 to 1.5 mg of calcium ions per unit of factor VIII is appropriate.

Other buffering and modifying agents may also be present in the dried material for reconstitution to the injection solution, for example histidine. However, we have found that the level of salts, particularly sodium chloride, present can affect the preservation on drying. It is thought desirable for the commercial product for injection to have an isotonic salt concentration. However, the processing formulations which are freeze-dried are desirably hypertonic, typically containing about 500 mM NaCl (isotonic NaCl=150 mM), as this is considered to help stabilise the blood factor. As a result, commercial freeze-dried formulations generally have a high salt content and are reconstituted for injection with the appropriate amount of sterile water to obtain an isotonic solution.

A considerably reduced salt content is preferred for the dried material of the invention and, in general a solution of about 500 units of Factor VIII per ml to be dried should preferably contain less than 200 mM e.g. 75 to 150 mM, NaCl, especially about 100 mM, or even lower, e.g. 20 to 50 mM, especially about 22 to 30 mM. Low salt preparations possess a higher dry stability. The dried product can be reconstituted to the desired salt level with a saline solution instead of the conventional water. In general, the molar ratio of trehalose to salt should be above 1:1, especially above 2.5:1 e.g. above 10:1, preferably above 12.5:1.

The dried composition may be obtained by drying an appropriate solution of the blood factor containing the correct proportions of trehalose and other desired components. In general, the solution that is dried should simply contain all the components required in the reconstituted injection solution, although the solution for drying may not necessarily be at the same dilution. Typically, the solution for drying will contain from 1 to 1000 units of factor VIII per ml. The methods of drying may include freeze drying, vacuum drying and spray-drying. A particularly preferred method according to the invention comprises vacuum drying at a temperature no greater than 25° C., preferably no greater than 10° C., to form a foam, thus maximising the exposed surface and the drying effect.

The following examples illustrate the invention further.

EXAMPLE 1

Recombinant factor VIII was received as a deep frozen solution containing approximately 2000 to 2500 units/ml in the manufacturer's high salt buffer. The thawed solution was dialysed against a buffer solution containing 500 mM NaCl, 15 mM $CaCl_2$ and 10 mM histidine at pH 6.8. The dialysed protein was diluted in the same buffer, but with added trehalose to give a final concentration of 500 units per ml and 10% by weight trehalose at pH 6.8. This solution was vacuum dried in 1 ml aliquots. Vacuum was reduced step-wise from atmospheric to 4 Pa (30 mTorr) to avoid freezing the sample. The temperature of the sample was not allowed to rise above 12° C. until the formation of a foam, after which the temperature was kept below 30° C. Total drying times were 24 to 28 hours.

The samples were stored for 0, 1.5, 3 and 6 months at 40° C. and then reconstituted in 5 ml aliquots of sterile distilled water before being tested for activity. The results are shown in the following table in comparison with a commercial freeze-dried product containing HSA. Both the test and commercial samples have a high salt content. The post-drying results show that with trehalose it is possible to dry factor VIII successfully in the absence of HSA, but that a high salt content is unsatisfactory for long term storage, even in the presence of HSA.

| Percentage of initial activity | | |
| --- | --- | --- |
| Time (months) | Sample | Commercial Product |
| 0 | 100.0 | 100.0 |
| 1.5 | 86.8 | 95.3 |
| 3 | 75.1 | 71.2 |
| 6 | 76.6 | 63.6 |

EXAMPLE 2

Samples were dried as described in Example 1 but using a buffer formulation comprising 100 mM NaCl, 15 mM $CaCl_2$, 15 mM histidine and 1.27 molar trehalose (48%) and stored at 60° C. before reconstitution. The results are given in the following table, in which the activity is measured on an ACL 100 automated coagulometer (Instrumentation Laboratory SpA, Milan, Italy). The test sample, with a low salt content showed no significant loss of activity on storage, even after four weeks of 60° C.

| Percentage of initial activity recovered | |
| --- | --- |
| Wet control | 100.0 |
| Post-drying | 95.5 |
| Two weeks | 96.0 |
| Four weeks | 96.8 |

EXAMPLE 3

Two formulations were prepared containing different salt concentrations as shown:

| Formulation A | | Formulation B | |
| --- | --- | --- | --- |
| NaCl | 0.13% | NaCl | 1.03% |
| $CaCl_2$ | 0.011% | $CaCl_2$ | 0.011% |
| L-histidine | 0.12% | L-histidine | 0.12% |
| Tris | 0.002% | Tris | 0.002% |
| Tween 80 | 0.002% | Tween 80 | 0.002% |
| PEG 3350 | 0.004% | PEG 3350 | 0.004% |
| Trehalose | 7.5% | Trehalose | 7.5% |
| Factor VIII | 50 U/ml | Factor VIII | 50 U/ml |
| Water to 100% | | Water to 100% | |

10 ml portions of the formulations were dispensed into separate 30 ml vials so as to give a concentration of factor VIII of 500 units/vial.

Freeze-drying was performed in a Laconco (Lyph-lock 12 stoppering) freeze drier. Initially, the samples were cooled to −40° C. and then placed under vacuum, before being warmed to −35° C. After 80 hours, the samples were warmed at a rate of 2.5° C./h until the shelf temperature reached 25° C. The samples were then kept at 25° C. for two hours before being sealed under vacuum and removed from the drier. After drying, the samples were rehydrated with 10 ml of water and the concentration of factor VIII was measured twice (Assays 1 and 2). The results are given in the following table and are expressed as a percentage of the concentration of Factor VIII with respect to the prefill control (which had been frozen at −70° C.). From the results shown, it can be concluded that Factor VIII can be successfully freeze dried in a trehalose based formulation in the absence of HSA.

| Sample | Assay 1 | Assay 2 |
| --- | --- | --- |
| Formulation A | 77% | 85% |
| Formulation B | 91% | 94% |

I claim:

1. A vial containing a dried native Factor VIII composition comprising a Factor VIII-stabilizing amount of trehalose and no albumin, the composition being
    (a) stable without refrigeration, and
    (b) suitable for reconstitution with water or with an aqueous solution for administration to a hemophilic patient by injection.

2. The composition of claim 1, containing 0.15 to 2.5 mg trehalose per unit of Factor VIII.

3. The composition of claim 1, wherein said native Factor VIII is recombinant.

4. The composition of claim 1, containing 1.0 to 1.5 mg $Ca^{2+}$ per unit of Factor VIII.

5. The composition of claim 1, wherein the composition comprises salt and the molar ratio of trehalose to the salt is above 1:1.

6. The composition of claim 5, containing more than 2.5 moles trehalose per mole of salt.

7. The composition of claim 6, containing more than 10 moles trehalose per mole of salt.

8. A process for preparing the dried native Factor VIII composition defined in claim 1 which
    process comprises drying a solution of native Factor VIII and trehalose in the absence of albumin.

9. The process of claim 8, wherein the drying is done at a temperature of no greater than 10° C.

10. The process of claim 9, wherein the drying is freeze-drying.

11. The process of claim 8, wherein an aliquot of the solution is placed in a vial and is freeze-dried.

12. A method for preparing a Factor VIII therapeutic composition for administration to a patient wherein the method comprises reconstituting the composition defined in claim 1 to obtain a solution that is suitable for injection.

13. The method of claim 12, wherein the reconstituting with water.

14. The method of claim 12, wherein the reconstituting is with saline.

* * * * *

UNITED STATES PATENT AND TRADEMARK OFFICE
CERTIFICATE OF CORRECTION

PATENT NO.        : 7,244,825 B2
APPLICATION NO.   : 10/658219
DATED             : July 17, 2007
INVENTOR(S)       : Bruce J. Roser It is certified that error appears in the above-identified patent and that said Letters Patent is hereby corrected as shown below:

In Claim 2, please make the following corrections:
  At column 4, line 27:
  2. The "composition" --vial-- of claim 1, containing 0.15 to 2.5 mg trehalose per unit of Factor VIII.

In Claim 3, please make the following corrections:
  At column 4, line 29:
  3. The "composition" --vial-- of claim 1, wherein said native Factor VIII is recombinant.

In Claim 4, please make the following corrections:
  At column 4, line 31:
  4. The "composition" --vial-- of claim 1, containing 1.0 to 1.5 mg $Ca^{2+}$ per unit of Factor VIII.

In Claim 5, please make the following corrections:
  At column 4, line 33:
  5. The "composition" --vial-- of claim 1, wherein the composition comprises salt and the molar ratio of trehalose to the salt is above 1:1.

In Claim 6, please make the following corrections:
  At column 4, line 36:

6. The "composition" --vial-- of claim 5, containing more than 2.5 moles trehalose per mole of salt.

UNITED STATES PATENT AND TRADEMARK OFFICE
CERTIFICATE OF CORRECTION

PATENT NO. : 7,244,825 B2
APPLICATION NO. : 10/658219
DATED : July 17, 2007
INVENTOR(S) : Bruce J. Roser It is certified that error appears in the above-identified patent and that said Letters Patent is hereby corrected as shown below:

<u>In Claim 7</u>, please make the following corrections:

<u>At column 4, line 38</u>:

7. The "composition" --vial-- of claim 6, containing more than 10 moles trehalose per mole of salt.

Signed and Sealed this

Twenty-second Day of July, 2008

JON W. DUDAS
*Director of the United States Patent and Trademark Office*